(12) United States Patent
Hall et al.

(10) Patent No.: US 10,062,370 B1
(45) Date of Patent: Aug. 28, 2018

(54) IMPEDANCE MATCHING TOILET SEAT

(71) Applicants: David R. Hall, Provo, UT (US); Dan Allen, Springville, UT (US); Ben Swenson, Lehi, UT (US); Justin R. Robinson, Provo, UT (US)

(72) Inventors: David R. Hall, Provo, UT (US); Dan Allen, Springville, UT (US); Ben Swenson, Lehi, UT (US); Justin R. Robinson, Provo, UT (US)

( * ) Notice: Subject to any disclaimer, the term of this patent is extended or adjusted under 35 U.S.C. 154(b) by 4 days.

(21) Appl. No.: 15/392,552

(22) Filed: Dec. 28, 2016

(51) Int. Cl.
| | | |
|---|---|---|
| *A47K 13/00* | (2006.01) | |
| *G10K 11/02* | (2006.01) | |
| *A47K 13/30* | (2006.01) | |
| *A47K 13/24* | (2006.01) | |
| *G01N 29/28* | (2006.01) | |
| *G01K 13/00* | (2006.01) | |

(52) U.S. Cl.
CPC .............. *G10K 11/02* (2013.01); *A47K 13/24* (2013.01); *A47K 13/305* (2013.01); *G01N 29/28* (2013.01); *G01K 13/00* (2013.01); *G01N 2291/02475* (2013.01)

(58) Field of Classification Search
CPC ....................................................... A47K 13/00
USPC ...................................................... 4/237–241
See application file for complete search history.

(56) References Cited

U.S. PATENT DOCUMENTS

| | | | | |
|---|---|---|---|---|
| 2013/0046477 A1* | 2/2013 | Hyde | ................... | A61B 5/073 702/19 |
| 2015/0294067 A1* | 10/2015 | Kare | ................... | G06F 19/322 705/3 |
| 2015/0294085 A1* | 10/2015 | Kare | ................... | G06F 19/3481 705/3 |
| 2015/0294086 A1* | 10/2015 | Kare | ................... | G06F 19/3481 705/3 |

\* cited by examiner

*Primary Examiner* — Lori Baker

(57) ABSTRACT

The novel impedance matching toilet seat apparatus in general, includes a cavity, an acoustic transducer, orifices, and an impedance matching substance dispenser. The cavity is positioned on a top surface of the toilet seat. The acoustic transducer is positioned within the cavity. The orifices are positioned on the top surface adjacent the acoustic transducer. The impedance matching substance dispenser is within an interior portion of the toilet seat. The dispenser includes a reservoir, a conduit, and a pump. The reservoir contains an impedance matching substance and is connected to the conduit and pump. The conduit fluidly connects the reservoir to the orifices.

20 Claims, 10 Drawing Sheets

IMPEDANCE MATCHING TOILET SEAT

BACKGROUND

Field of the Invention

This invention relates generally to the field of medical toilets, and more specifically to impedance matching acoustic transduction toilet seats.

SUMMARY OF THE INVENTION

An invention has been developed in response to present state of the art and, in particular, in response to problems and needs in the art that have not yet been fully solved by currently available systems and methods. Accordingly, an impedance matching toilet seat has been developed. Features and advantages of different embodiments of the invention will become more fully apparent from the following description and appended claims, or may be learned by practice of the invention as set forth hereinafter.

A toilet seat apparatus is disclosed herein which, in general, includes a cavity, an acoustic transducer, orifices, and an impedance matching substance dispenser. The cavity is positioned on a top surface of the toilet seat. The acoustic transducer is positioned within the cavity. The orifices are positioned on the top surface adjacent the acoustic transducer. The impedance matching substance dispenser is within an interior portion of the toilet seat. The dispenser includes a reservoir, a conduit, and a pump. The reservoir contains an impedance matching substance and is connected to the conduit and pump. The conduit fluidly connects the reservoir to the orifices.

The toilet seat may include multiple cavities positioned on the top surface of the toilet seat, and may include multiple acoustic transducers positioned within the cavities. The pump may include one or more valves. The reservoir may include one or more valves; if so, one of the one or more valves may be an impedance matching substance refilling port. The conduit may include a valve. The toilet may include temperature sensors.

The dispenser may include a heat exchanger. The heat exchanger may be thermally coupled to the conduit. The heat exchanger may be thermally coupled to the reservoir. Sections of the conduit may pass through the heat exchanger.

The dispenser may include a heater. The heater may be a resistance heater adjacent the conduit. The heater may be an inductive heater, and the inductive heater may include a ferromagnetic core positioned within the conduit. The heater may be a direct current resistive heater with a heat exchanger thermally coupled to the heater.

The toilet seat may include a resistive heater embedded in the toilet seat. The toilet seat may include a controller. The controller may be electrically coupled to the acoustic transducer and the pump. The toilet seat may also include motion sensors. The motion sensors may be electrically coupled to the controller and positioned on the top surface of the toilet seat. The toilet seat may include a light transceiver, which may be electrically coupled to the controller and may be positioned on the top surface of the toilet seat. The toilet seat may include a wireless transceiver which may be electrically coupled to the controller.

BRIEF DESCRIPTION OF THE DRAWINGS

A more particular description of the invention briefly described above is made below by reference to specific embodiments. Several embodiments are depicted in drawings included with this application, in which.

DETAILED DESCRIPTION

A detailed description of the claimed invention is provided below by example, with reference to embodiments in the appended figures. Those of skill in the art will recognize that the components of the invention as described by example in the figures below could be arranged and designed in a wide variety of different configurations. Thus, the detailed description of the embodiments in the figures is merely representative of embodiments of the invention, and is not intended to limit the scope of the invention as claimed.

Figure 1:
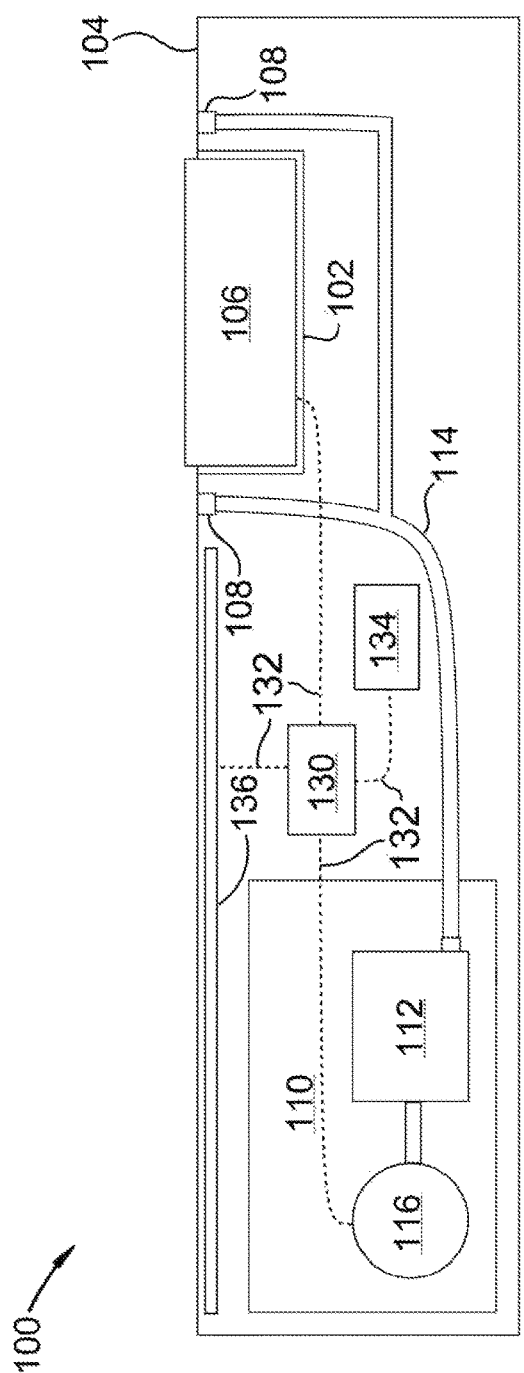
FIG. 1 depicts a cross-sectional view of a toilet seat apparatus.

FIG. 1 depicts a cross-sectional view of a toilet seat apparatus. Toilet seat apparatus 100 includes cavity 102, acoustic transducer 106, orifices 108, and impedance matching substance dispenser 110. Cavity 102 is positioned on a tope surface of toilet seat 100. Acoustic transducer 106 is positioned within cavity 102. Orifices 108 are positioned on top surface 104 adjacent acoustic transducer 106. Dispenser 110 is located within an interior portion of toilet seat 100. Dispenser 110 includes reservoir 112, conduit 114, and pump 116. Reservoir 112 contains an impedance matching substance. Reservoir 112 is connected to conduit 114 and pump 116. Conduit 114 fluidly connects reservoir 112 to orifices 108.

Gaps between walls of cavity 102 and walls of acoustic transducer 106 may include any of a variety of adhesives, such as natural rubber, polychloroprene, polyurethane, cyanoacrylate, or acrylic polymers, which may adhere acoustic transducer 106 to cavity 102. An adhesive could also be utilized for the purpose of sealing between acoustic transducer 106 and cavity 102 from moisture.

Acoustic transducer 106 may be level with top surface 104 or may be offset into or out of toilet seat 100. For example, in some embodiments, a user may sit on toilet seat 100, placing his or her thighs on top surface 104. Tissue of the user's thighs may sufficiently stiff such that his or her thigh may only touch acoustic transducer 106 while acoustic transducer 106 is offset out of toilet seat 100 by more than approximately 2 millimeters.

An impedance matching substance may be stored in reservoir 112. Pump 116 may create a pressure difference between reservoir 112 and atmospheric air such that a part of the impedance matching substance may flow through conduit 114 to orifices 108. Orifices 108 may subsequently inject the impedance matching substance onto a surface of acoustic transducer 106. A user may subsequently sit on toilet seat 100 and acoustic transducer 106.

Pump 116 may be any of a variety of pumps, including a screw pump, an impeller pump, a gear pump, a plunger pump, a piston pump, or a diaphragm pump. Pump 116 may be actuated manually, via a motor, via a linear actuator, or by some other means.

Toilet seat 100 may include controller 130. Controller 130 may be electrically coupled to acoustic transducer 106 and pump 116 via wiring 132. Pump 116 and acoustic transducer 106 may be actuated by controller 130. Controller 130 may send and receive acoustic data to/from acoustic transducer 106.

Toilet seat 100 may include wireless transceiver 134. Toilet seat 100 may also include resistive heater 136. Resistive heater 136 may be embedded in toilet seat 100 such that resistive heater 136 may heat toilet seat 100. Resistive heater 136 and wireless transceiver 134 may each be electrically coupled to controller 130 via wiring 132. Controller 130 may actuate resistive heater 136 and wireless transceiver 134. Controller 130 may send and receive communications via wireless transceiver 134. Controller 130, pump 116, wireless transceiver 134, acoustic transducer 106, and resistive heater 136 may be powered by a variety of means, including via a wall outlet, a battery, or solar panels.

In some embodiments, for example, a user may have a peripheral device which communicates with wireless transceiver 134. The peripheral device may be any of a variety of devices, including a smart phone, a laptop, a smart watch, etc. Wireless transceiver 134 may subsequently transfer data to controller 130 via wiring 132. Controller 130 may initiate a transduction sequence with a purpose of gathering and recording acoustic data from the user using toilet seat 100. The transduction sequence initiated by controller 130 may be put into effect or ended by a user via wireless communication of a peripheral device, via a button included on toilet seat 100, or via proximity of a user as detected by acoustic transducer 106. Controller 130 may send commands to pump 116 to actuate. Pump 116 may actuate, causing a pressure difference which may force an impedance matching substance to flow through conduit 114 to orifices 108. Orifices 108 may subsequently inject the impedance matching substance onto a surface of acoustic transducer 106. Controller 130 may also send electrical signals to acoustic transducer 106. Acoustic transducer 106 may transduce the electrical signals into sound waves. Acoustic transducer 106 may also receive and send acoustic data in the form of electrical signals back to controller 130. Controller 130 may store the acoustic data in memory included in controller 130. Controller 130 may also send the acoustic data to a peripheral device of the user, a server, or a peripheral device of a physician to be stored and analyzed. The user may seat himself or herself on toilet seat 100. The impedance matching substance may connect acoustic transducer 106 to tissue of the user (such as skin on the user's thigh), allowing sound waves to propagate through tissue of the user effectively.

Orifices 108 may include covers which may be removed and reset manually or automatically. The covers may be actuated by controller 130 to automatically slide away from orifices 108 before, during, or after pump 116 is actuated. Removing covers before actuating pump 116 may be desirable in order to avoid impedance matching substance build up; however, it may also be desirable to remove covers from orifices 108 after pump 116 is actuated so that a larger pressure difference may be build up for the purpose of injecting fluid with a higher initial kinetic energy (so that the impedance matching substance may travel further when it is first injected). Pressure buildup and subsequent removal of covers from orifices 108 may be done automatically.

Acoustic transducer 106 may be actuated by way of a force sensor included in toilet seat 100 which may be positioned between a surface of cavity 102 and a surface of acoustic transducer 106. Acoustic transducer 106 may be actuated when a user sits upon acoustic transducer 106, developing a force in the force sensor.

An impedance matching substance which may be included in reservoir 112 may be any of a variety of fluids, including water, silica gel, a dielectric gel, etc. Conduit 114 may include any of a variety of materials, including copper, iron, galvanized steel, polyvinyl chloride (PVC), chlorinated polyvinyl chloride (CPVC), or cross-linked polyethylene (PEX). Additionally, conduit 114 may include insulation which may surround an outside surface of the piping in order to reduce heat exchange between conduit 114 and interior portions of toilet seat 100.

Figure 2:
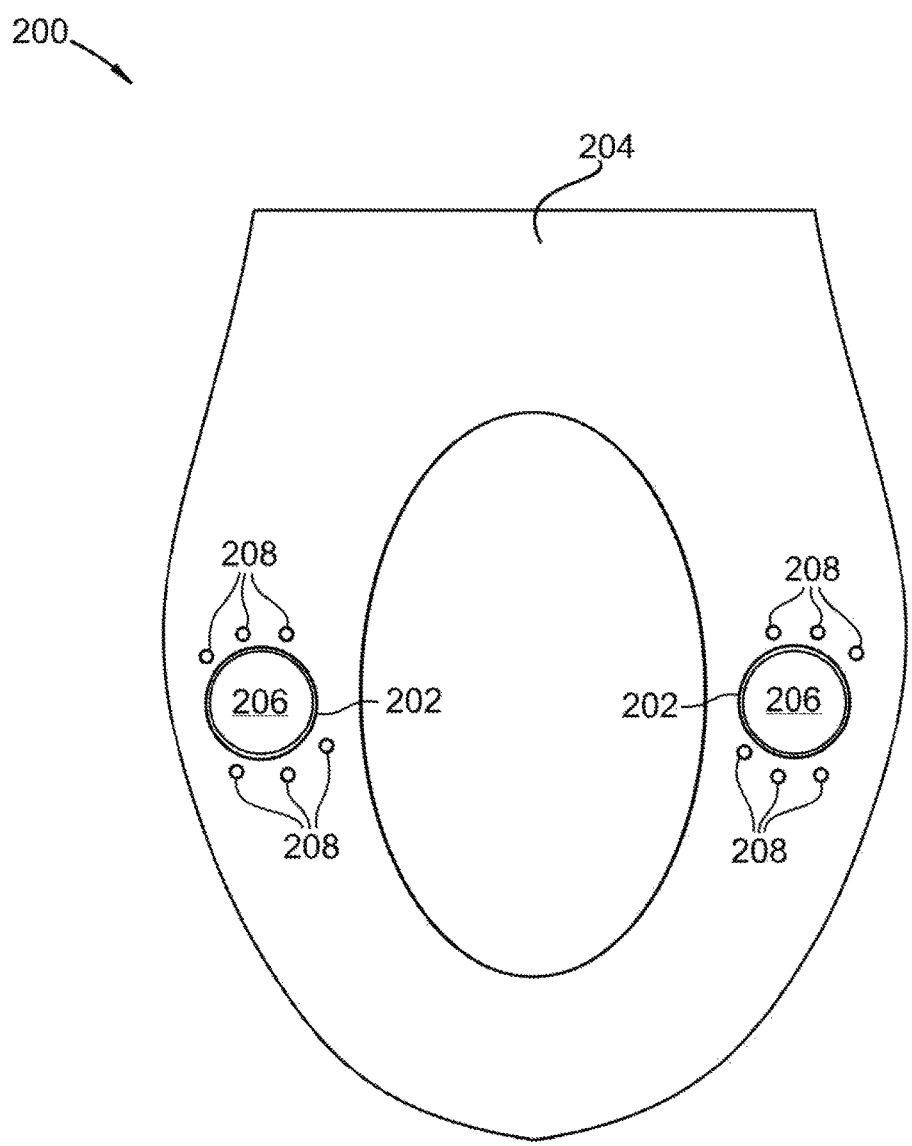
FIG. 2 depicts a top view of a toilet seat.

FIG. 2 depicts a top view of a toilet seat. Toilet seat apparatus 200 may include multiple cavities 202 and multiple acoustic transducers 206. The cavities 202 may be positioned on top surface 204 of toilet seat 200. Acoustic transducers 206 may be positioned within cavities 202.

Orifices 208 may be positioned on top surface 204. Each transducer of multiple transducers 206 may have one or more of orifices 208 adjacent it.

Figure 3:
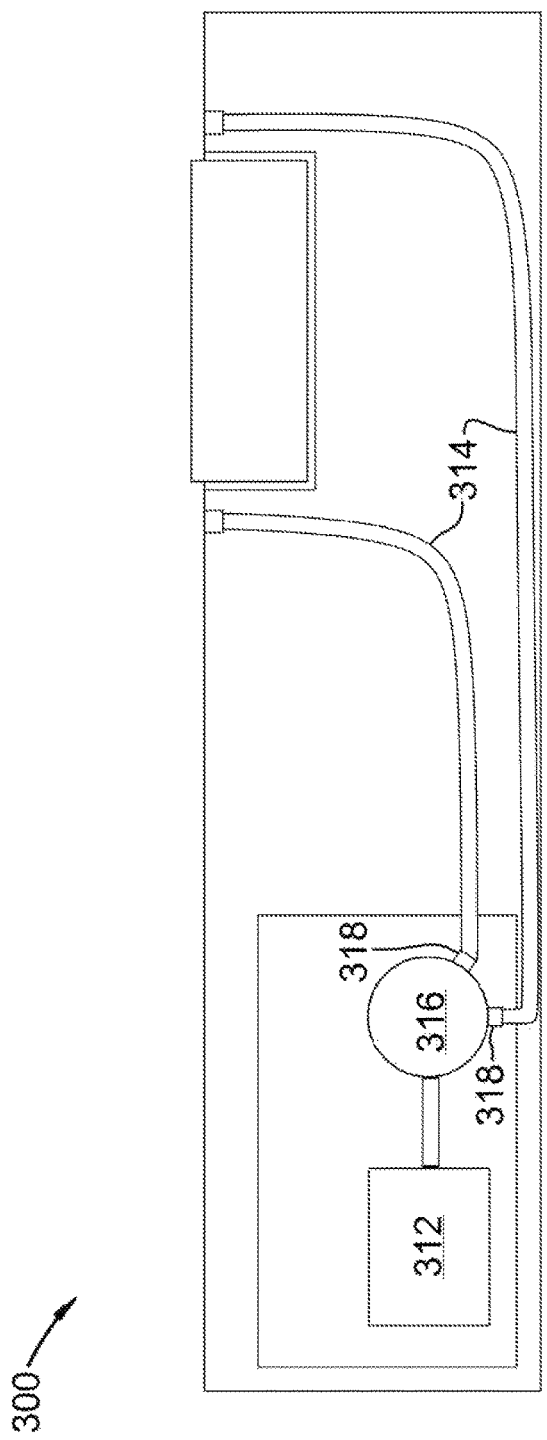
FIG. 3 depicts an embodiment similar to FIG. 1 with multiple conduits.

FIG. 3 depicts an embodiment similar to FIG. 1 with multiple conduits. Pump 316 of toilet seat apparatus 300 may include one or more valves 318. Valves 318 may connect pump 316 to one or more conduits 314. Reservoir 312 may be fluidly coupled to pump 316. When actuated, pump 316 may cause an impedance matching substance to flow from reservoir 312, through pump 316, subsequently through valves 318, and through conduits 314.

Pump 316 may include a force sensor, or a pressure sensor, which signals to pump 316 when internal pressure of the impedance matching substance rises above a predetermined level. In some embodiments, for example, a maximum pressure difference across valves 318, while valves 318 are closed, may be approximately equivalent to 20 pounds per square inch (psi). While valves 318 are closed, a pressure difference across valves 318 may reach 20 psi before valves 318 may open, allowing the impedance matching substance to flow through valves 318.

Each of valves 318 may have different maximum pressure differences.

Figure 4:
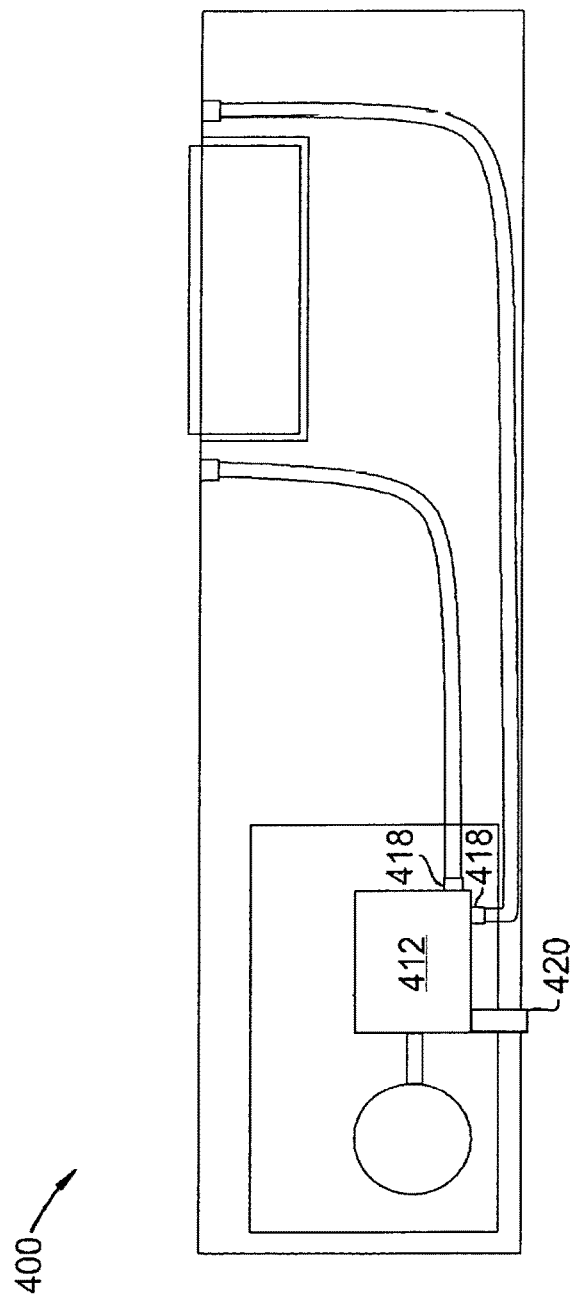
FIG. 4 depicts an embodiment similar to FIG. 3 with a refilling port.

FIG. 4 depicts an embodiment similar to FIG. 3 with a refilling port. Reservoir 412 of toilet seat apparatus 400 may include one or more valves 418. One of one or more valves 418 may be impedance matching substance refilling port 420. Reservoir 412 may be manually filled with an impedance matching substance (IMS) via refilling port 420. Refilling port 420 may be biased such that an IMS may flow through refilling port 420 into reservoir 412, however the IMS may be prevented from flowing in reverse by refilling port 420.

Refilling port 420 may be fluidly connected to an IMS supply, such that reservoir 412 may be refilled automatically.

Figure 5:
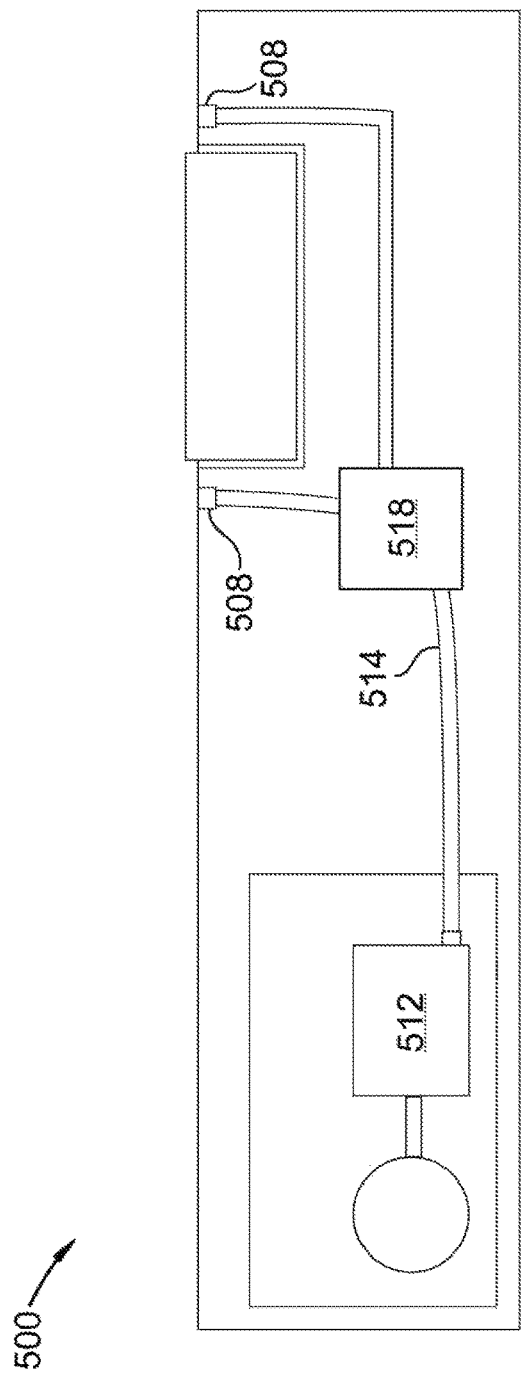
FIG. 5 depicts an embodiment similar to FIG. 1 with a valve.

FIG. 5 depicts an embodiment similar to FIG. 1 with a valve. Conduit 514 of toilet seat apparatus 500 may include valve 518. Valve 518 may direct an impedance matching substance as it flows through valve 518 through one or more branches in conduit 514. Valve 518 may also stop fluid flow between reservoir 512 and orifices 508 while toilet seat 500 is not in use.

Valve 518 may be opened and closed via solenoids or other active means, or valve 518 may be passively biased to fluid flow (in other words, valve 518 may allow fluid to flow through one way but not in reverse).

Figure 6:
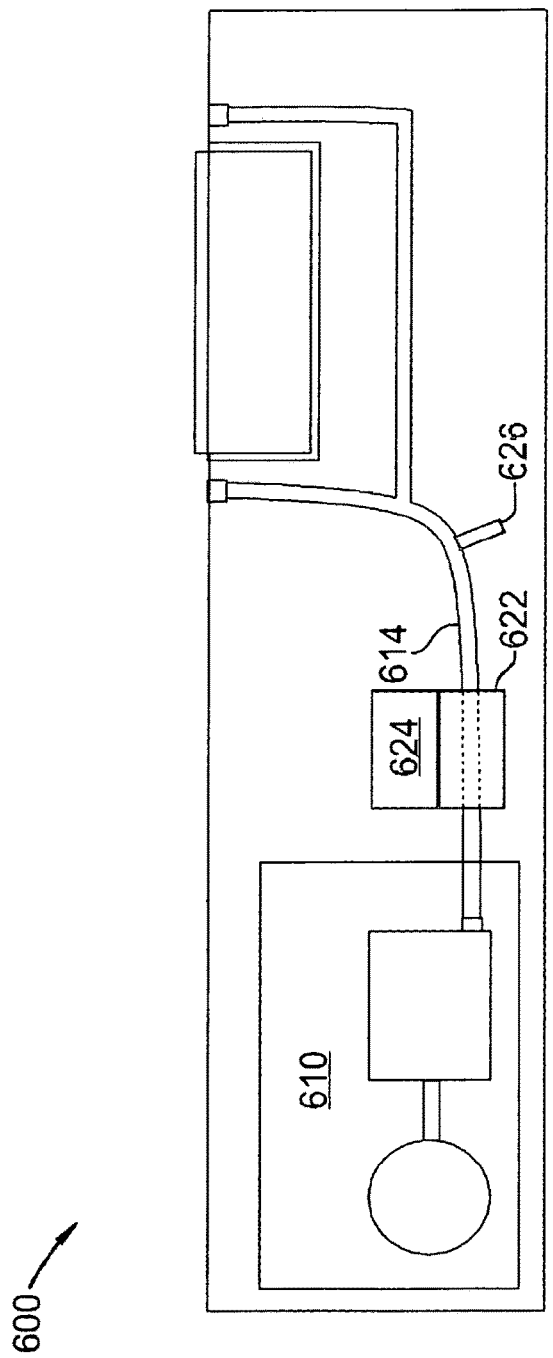
FIG. 6 depicts an embodiment similar to FIG. 1 with a heater.

FIG. 6 depicts an embodiment similar to FIG. 1 with a heater. Toilet seat apparatus 600 may include impedance matching substance dispenser 610. Dispenser 610 may include heater 624. Toilet seat 600 may also include temperature sensor 626. Heater 624 may be any of a variety of heaters, including an inductive heater, a direct current resistive heater, or a hot water heater. Heater 624 may heat an impedance matching substance (IMS) as the IMS flows through conduit 614. Temperature sensor 626 may be used to determine temperature of the IMS. Heater 624 may activate to add heat to the IMS or heater 624 may deactivate so that the IMS doesn't receive more heat from heater 624, depending on the temperature determined by temperature sensor 626.

In some embodiments, for example, a user may find it comfortable to have an IMS in contact with his or her skin if the IMS is between 97° F. and 101° F. Heater 624 may receive temperature information wirelessly or via wires from temperature sensor 626. Heater 624 may activate in response to flow of the IMS. When temperature sensor 626 reads a temperature above 101° F., heater 624 may decrease an average amount of heat transferred to the IMS and/or deactivate. While the IMS is flowing and if temperature sensor 626 reads a temperature below 97° F., heater 624 may activate and/or increase an average amount of heat transferred to the IMS. In this preceding manner the IMS may be maintained at temperatures consistent with the user's comfort preferences.

Dispenser 610 may also include heat exchanger 622. Heat exchanger 622 may be thermally coupled to conduit 614. Conduit 614 may include a section of copper pipe, which has high thermal conductivity in comparison with PVC, CPVC, PEX, etc. Heat exchanger 622 may be thermally coupled to conduit 614 efficiently by applying thermal grease or solder between a section of conduit 614 and heat exchanger 622. Sections of conduit 614 may pass through heat exchanger 622.

Heater 624 may be a direct current resistive heater and heat exchanger 622 may be thermally coupled to heater 624. Heat exchanger 622 may increase effectiveness of heat exchange between heater 624 and the IMS of conduit 614, where effectiveness is defined as a ratio of heat transfer achieved to maximum possible heat transfer. Heat exchanger 622 may be a shell-and-tube heat exchanger with the working fluid being an oil.

Figure 7:
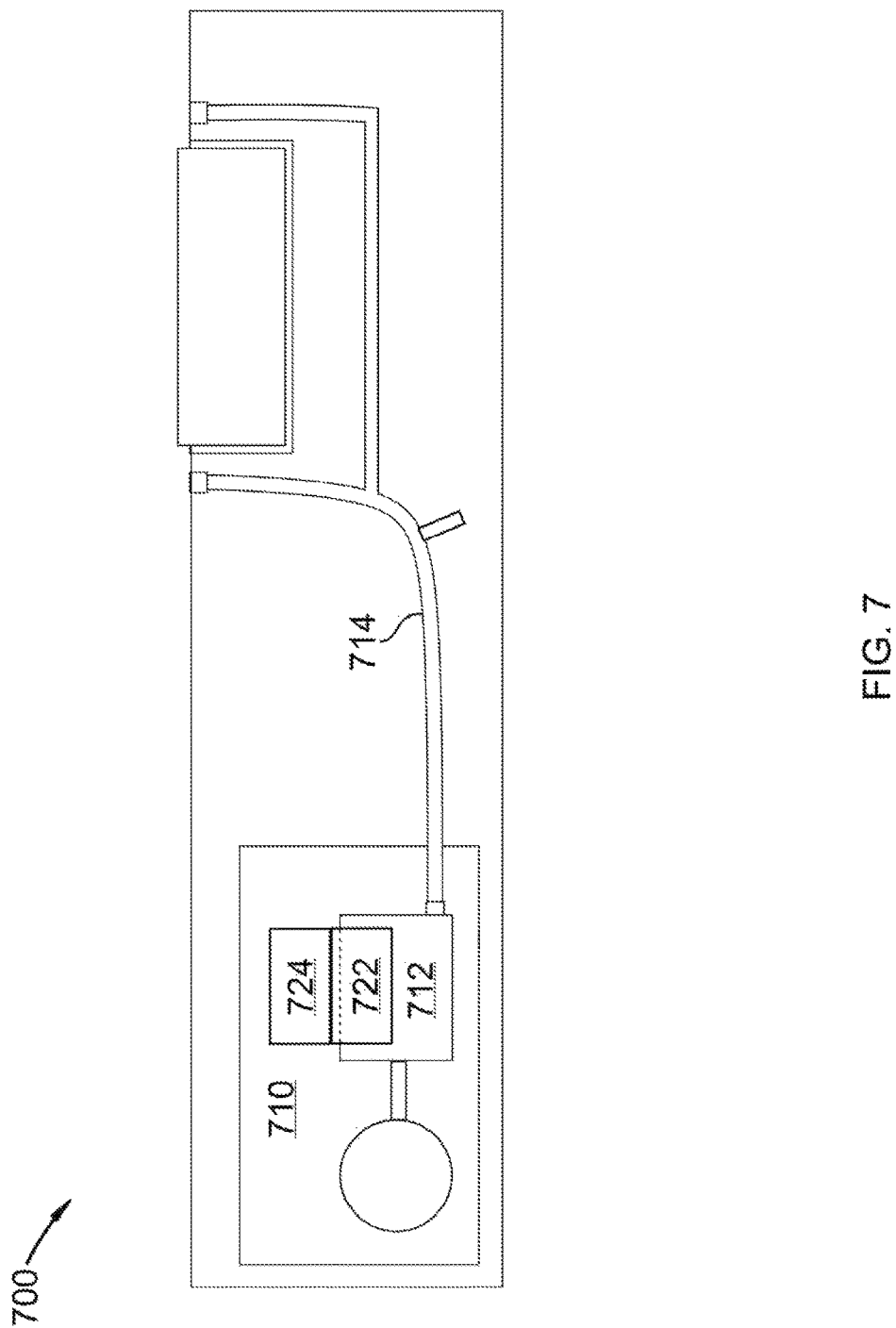
FIG. 7 depicts an embodiment similar to FIG. 6 with a heat exchanger coupled to a reservoir.

FIG. 7 depicts an embodiment similar to FIG. 6 with a heat exchanger coupled to a reservoir. Impedance matching substance dispenser 710 of toilet seat apparatus 700 may include heat exchanger 722. Heat exchanger 722 may be thermally coupled to reservoir 712. Heater 724 may also be thermally coupled to heat exchanger 722, and may thereby heat an impedance matching substance (IMS) contained within reservoir 712 before the IMS reaches conduit 714.

Figure 8:
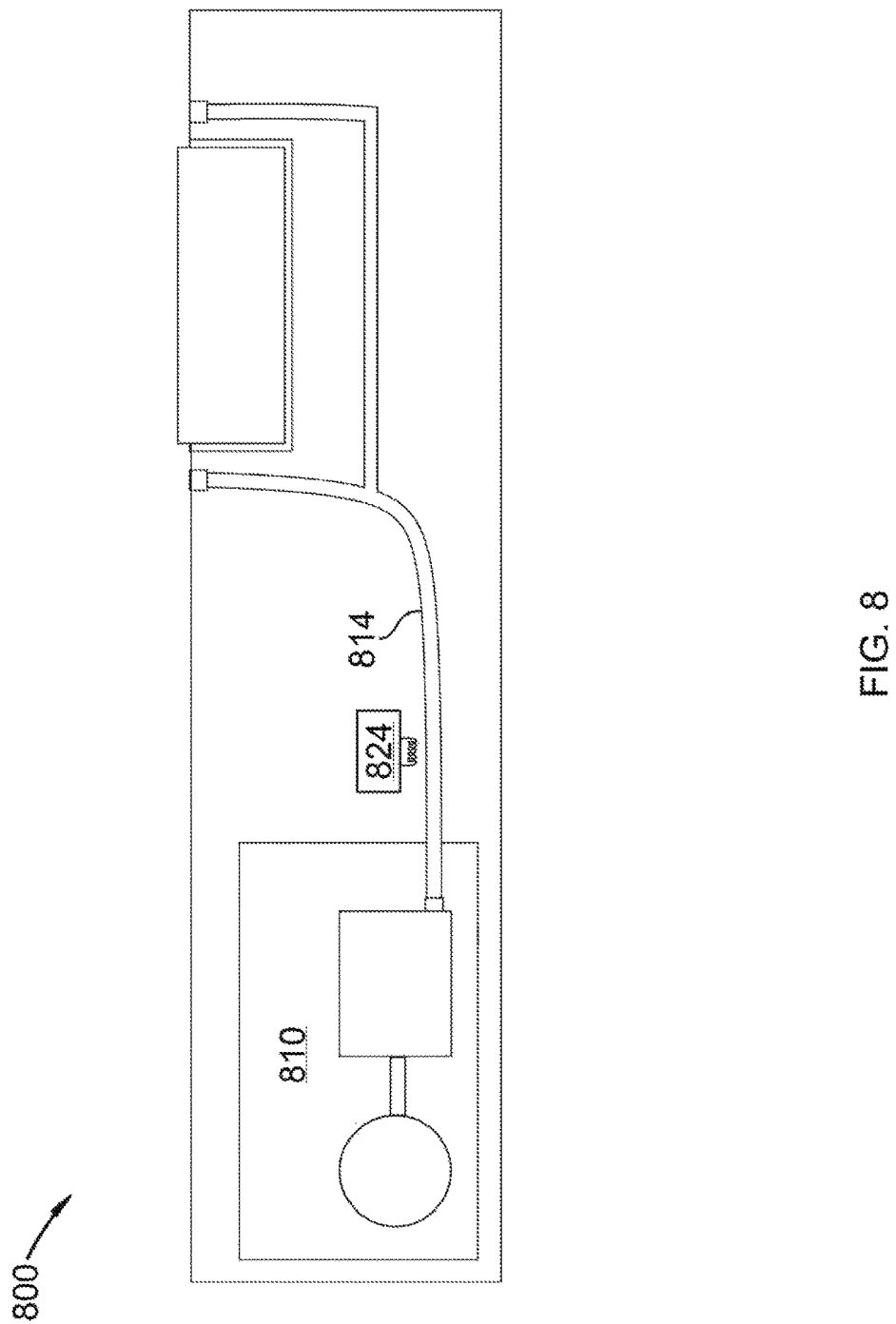
FIG. 8 depicts a side view of a toilet seat with a resistance heater inside.

FIG. 8 depicts a side view of a toilet seat with a resistance heater inside. Dispenser 810 of toilet seat apparatus 800 may include resistance heater 824. Heater 824 may be positioned adjacent conduit 814. Heater 824 may also be thermally coupled to conduit 814 to increase effectiveness of heat transfer.

Figure 9:
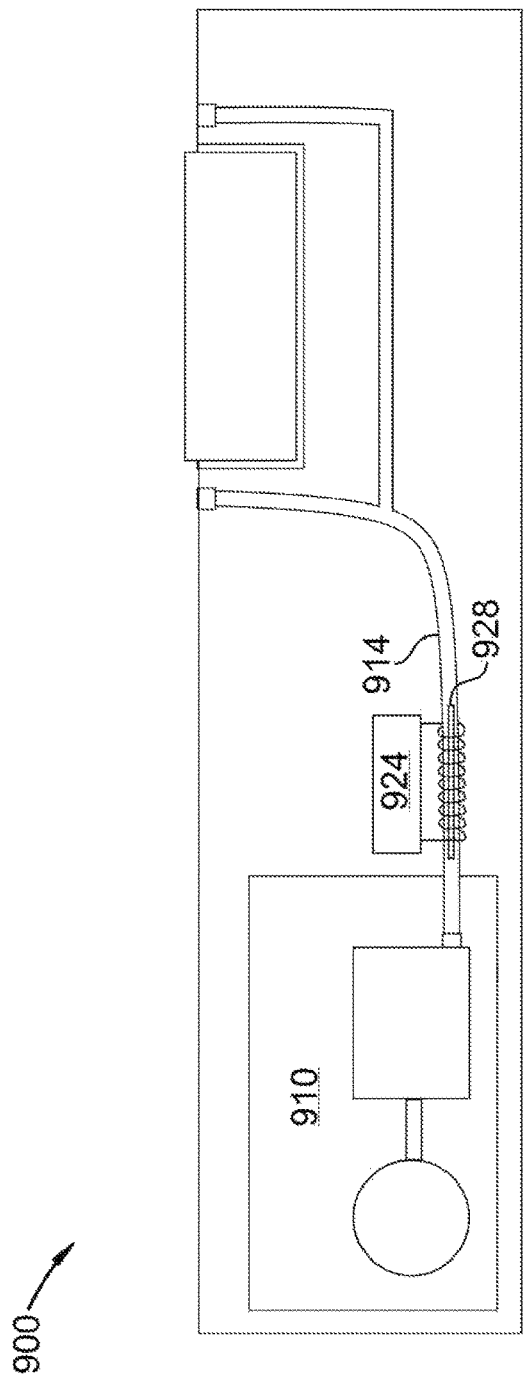
FIG. 9 depicts an embodiment similar to FIG. 8 with an induction heater.

FIG. 9 depicts an embodiment similar to FIG. 8 with an induction heater. Dispenser 910 of toilet seat apparatus 900 may include inductive heater 924. Heater 924 may include ferromagnetic core 928 positioned within conduit 914. Heater 924 may include inductive coils surrounding a portion of conduit 914 concentric with core 928. Electric current may alternate across the inductive coils of heater 924 at a frequency which is dependent on the size and material of core 928 used. The frequency used may range from 30 kHz down to 5 kHz, decreasing for thicker core 928 and desired temperature.

In place of or in addition to core 928, conduit 914 may include a portion of ferromagnetic material where heater 924 is positioned surrounding conduit 914.

Figure 10:
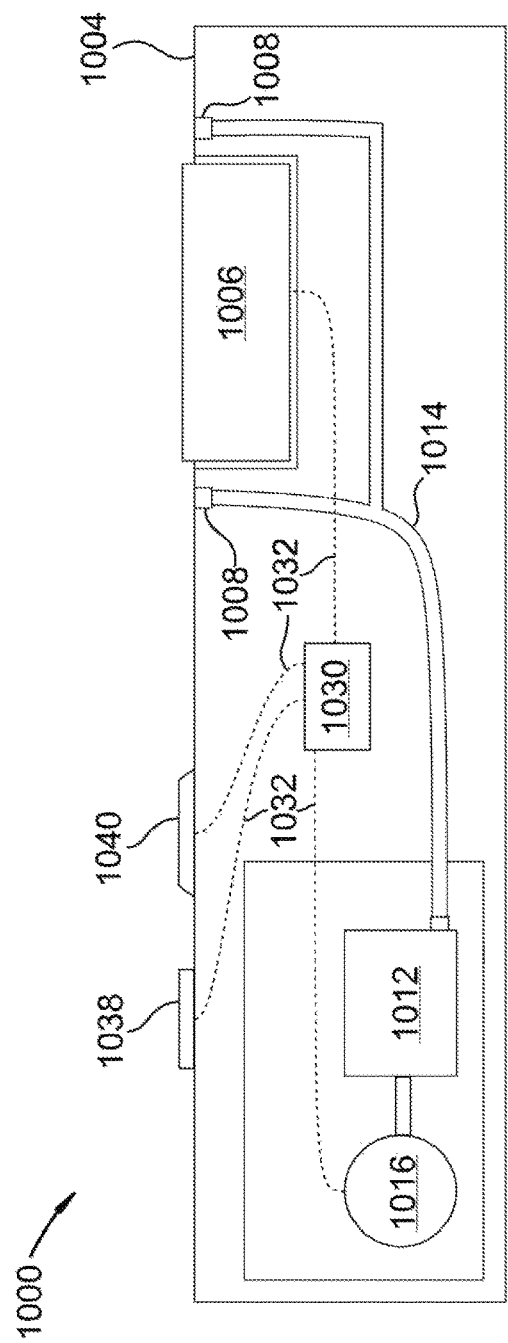
FIG. 10 depicts an embodiment similar to FIG. 1 with a sensor.

FIG. 10 depicts an embodiment similar to FIG. 1 with a sensor. Toilet seat apparatus 1000 may include motion sensor 1038. Motion sensor 1038 may be positioned on top surface 1004 of toilet seat 1000. Motion sensor 1038 may be electrically coupled to controller 1030 wirelessly or via wires 1032.

Toilet seat 1000 may include light transceiver 1040. Light transceiver 1040 may be positioned on top surface 1004. Light transceiver 1040 may be electrically coupled to controller 1030 wirelessly or via wires 1032.

In some embodiments, for example, a user may walk towards and begin sitting on toilet seat 1000. Motion sensor 1038, light transceiver 1040, or a combination thereof may sense proximity or motion of the user and may send data to controller. Controller 1030 may signal to pump 1016 to actuate. Pump 1016 subsequently may cause an impedance matching substance (IMS) to flow out of reservoir 1012 and through conduit 1014 to orifices 1008. As orifices 1008 receive the IMS, orifices 1008 may inject the IMS onto a surface of acoustic transducer 1006. Simultaneously, acoustic transducer 1006, which may be electrically coupled to controller 1030, may receive electrical signals, transduce those signals into acoustic signals (sending the acoustic signals into tissue of the user), receive reflected acoustic signals, and transduce those acoustic signals into electrical signals (sent back to controller 1030).

The invention claimed is:
1. A toilet seat apparatus comprising:
a cavity positioned on a top surface of the toilet seat;
an acoustic transducer positioned within the cavity;
orifices positioned on the top surface adjacent the acoustic transducer;
an impedance matching substance dispenser within an interior portion of the toilet seat, wherein the dispenser comprises a reservoir containing an impedance matching substance, the reservoir connected to a conduit and a pump; and
wherein the conduit fluidly connects the reservoir to the orifices.

2. The toilet seat apparatus of claim 1, comprising multiple cavities positioned on the top surface of the toilet seat with multiple acoustic transducers positioned within the cavities.

3. The toilet seat apparatus of claim 1, wherein the pump comprises one or more valves.

4. The toilet seat apparatus of claim 1, wherein the reservoir comprises one or more valves.

5. The toilet seat apparatus of claim 4, wherein one of the one or more valves is an impedance matching substance refilling port.

6. The toilet seat apparatus of claim 1, wherein the conduit comprises a valve.

7. The toilet seat apparatus of claim 1, wherein the dispenser further comprises a heater.

8. The toilet seat apparatus of claim 7, further comprising a temperature sensor.

9. The toilet seat apparatus of claim 7, wherein the dispenser comprises a heat exchanger.

10. The toilet seat apparatus of claim 9, wherein the heat exchanger is thermally coupled to the conduit.

11. The toilet seat apparatus of claim 9, wherein the heat exchanger is thermally coupled to the reservoir.

12. Toilet seat apparatus of claim 9, wherein sections of the conduit pass through the heat exchanger.

13. The toilet seat apparatus of claim 7, wherein the heater is a resistance heater adjacent the conduit.

14. The toilet seat apparatus of claim 7, wherein the heater is an inductive heater comprising a ferromagnetic core positioned within the conduit.

15. The toilet seat apparatus of claim 9, wherein the heater is a direct current resistive heater and the heat exchanger is thermally coupled to the heater.

16. The toilet seat apparatus of claim 1, further comprising a resistive heater embedded in the toilet seat.

17. Toilet seat apparatus of claim 1, further comprising a controller electrically coupled to the acoustic transducer and the pump.

18. Toilet seat apparatus of claim 17, further comprising motion sensors electrically coupled to the controller and positioned on the top surface of the toilet seat.

19. Toilet seat apparatus of claim 17, further comprising a light transceiver which is electrically coupled to the controller and positioned on the top surface of the toilet seat.

20. Toilet seat apparatus of claim 17, further comprising a wireless transceiver electrically coupled to the controller.

* * * * *